United States Patent [19]

Weissman

[11] Patent Number: 4,708,648

[45] Date of Patent: * Nov. 24, 1987

[54] DENTAL MODEL PROTECTIVE CARRIER

[75] Inventor: Bernard Weissman, New York, N.Y.

[73] Assignee: IPCO Corporation, White Plains, N.Y.

[*] Notice: The portion of the term of this patent subsequent to Sep. 3, 2002 has been disclaimed.

[21] Appl. No.: 832,305

[22] Filed: Feb. 24, 1986

[51] Int. Cl.$^4$ .............................................. A61C 19/00
[52] U.S. Cl. ........................................ 433/49; 433/34; 433/74
[58] Field of Search .................. 433/34, 74, 60, 49

[56] References Cited

U.S. PATENT DOCUMENTS

| | | | |
|---|---|---|---|
| 3,702,027 | 11/1972 | Marshall et al. | 433/49 |
| 4,439,151 | 3/1984 | Whelan | 433/60 |
| 4,538,987 | 9/1985 | Weissman | 433/34 |

FOREIGN PATENT DOCUMENTS 2835094  2/1980 Fed. Rep. of Germany ........ 433/49

Primary Examiner—John J. Wilson
Assistant Examiner—Adriene J. Lepiane
Attorney, Agent, or Firm—Goodman & Teitelbaum

[57] ABSTRACT

A protective carrier for a dental model including a tray portion hinged to a cover portion, a recessed cavity being provided in the tray portion to receive the pedestal part of the dental model. An arcuate rib member is removably coupled onto the tray portion and overhangs the cavity of the tray portion to thereby engage a ledge provided on the dental model to securely retain the dental model within the cavity. A recessed chamber is provided in the cover portion to mate with the cavity in the tray portion to define a closed compartment for the dental model.

19 Claims, 10 Drawing Figures 4,708,648

DENTAL MODEL PROTECTIVE CARRIER

BACKGROUND OF THE INVENTION

This invention relates to dental models, and more particularly to a protective carrier for securely retaining a dental model therein.

In the production of tooth crowns, bridges and other dental prostheses, it is a general dental procedure to form a model for use in the formation of the prosthesis. The production of such dental model requires many complex and time consuming steps. It usually begins with an imprint of the prepared teeth and related portions. The imprint is then filled with a special plaster mass from which mold cavities can be formed. The production is quite involved requiring effort both by the dentist and the laboratory where transportation, storage, shipping and movement of the dental model is usually necessary. Care must therefore be taken to prevent impairing the dental model which would require additional time and effort to replace. The model, which is usually stone, must be maintained in a usable condition without any cracking or chipping thereof.

Dental models usually include special keying arrangements to permit frequent removal and insertion of the dental model and sections thereof into a die tray. The key arrangements are cast into the pedestal portion of the dental model to permit proper seating of the dental model, thereby avoiding any damaging of the model.

There is, accordingly, a need for a protective device or carrier which can hold the dental model during storage and transport. The carrier must be one that can accommodate any keyed arrangement cast into the dental model, so that the dental model will appropriately fit into the carrier and be properly seated.

While the protective carrier must be one that will retain the dental model in place, at the same time, it must facilitate removal of the dental model when the model must be worked on or used for further processing.

SUMMARY OF THE INVENTION

Accordingly, it is an object of the present invention to provide a protective device for holding a dental model for storage and transport of the dental model, thereby avoiding damage to the model.

Another object of the present invention is to provide a carrier for a dental model which permits the model to be securely retained within the carrier.

Yet a further object of the present invention is to provide a dental model carrier which includes a cavity for receiving the dental model, and has a keyed seat for matingly receiving a corresponding keyed pedestal portion of the dental model.

Still another object of the present invention is to provide a dental model carrier which can be used for retaining the dental model while permitting access for further molding operations.

Yet another object of the present invention is to provide a dental model carrier having a removable retaining member for securing the dental model in the carrier.

Briefly, in accordance with the present invention, there is provided a protective carrier for a dental model, wherein the model is of a type which is used to produce a dental prosthesis. The carrier includes a tray portion having a recessed cavity for receiving a pedestal part of the model. A retaining member is removably coupled onto the tray portion for securing the dental model in the cavity. A cover portion is hinged to the tray portion and includes a recessed chamber. The cover portion is closed onto the tray portion, whereby the recessed chamber and the cavity together provide a closed compartment for the dental model, so that the dental model can thereby be securely moved and transported within the carrier.

In an embodiment of the present invention, the retaining member is in the form of an arcuate U-shaped rib which partially projects over the recessed cavity to thereby engage a ledge provided on the dental model, thereby retaining the dental model in the cavity. Suitable locking tabs are placed at the distal ends of the arcuate rib which mate into receiving slots in the tray portion. At the medial section of the arcuate rib there is provided a positioning tab which holds the retaining rib in place as it is being locked onto the tray portion, and also secures the retaining rib in the locked position.

Once the dental model is locked in place by the retaining rib, the cover portion is closed onto the tray portion and locked in place so that the model can be carried, transported, and stored.

BRIEF DESCRIPTION OF THE DRAWINGS

With the above and additional objects and advantages in view, as will hereinafter appear, this invention comprises the devices, combinations and arrangements of parts hereinafter described by way of example, and illustrated in the accompanying drawings of a preferred embodiment in which.

DESCRIPTION OF THE PREFERRED EMBODIMENT

Figure 1:
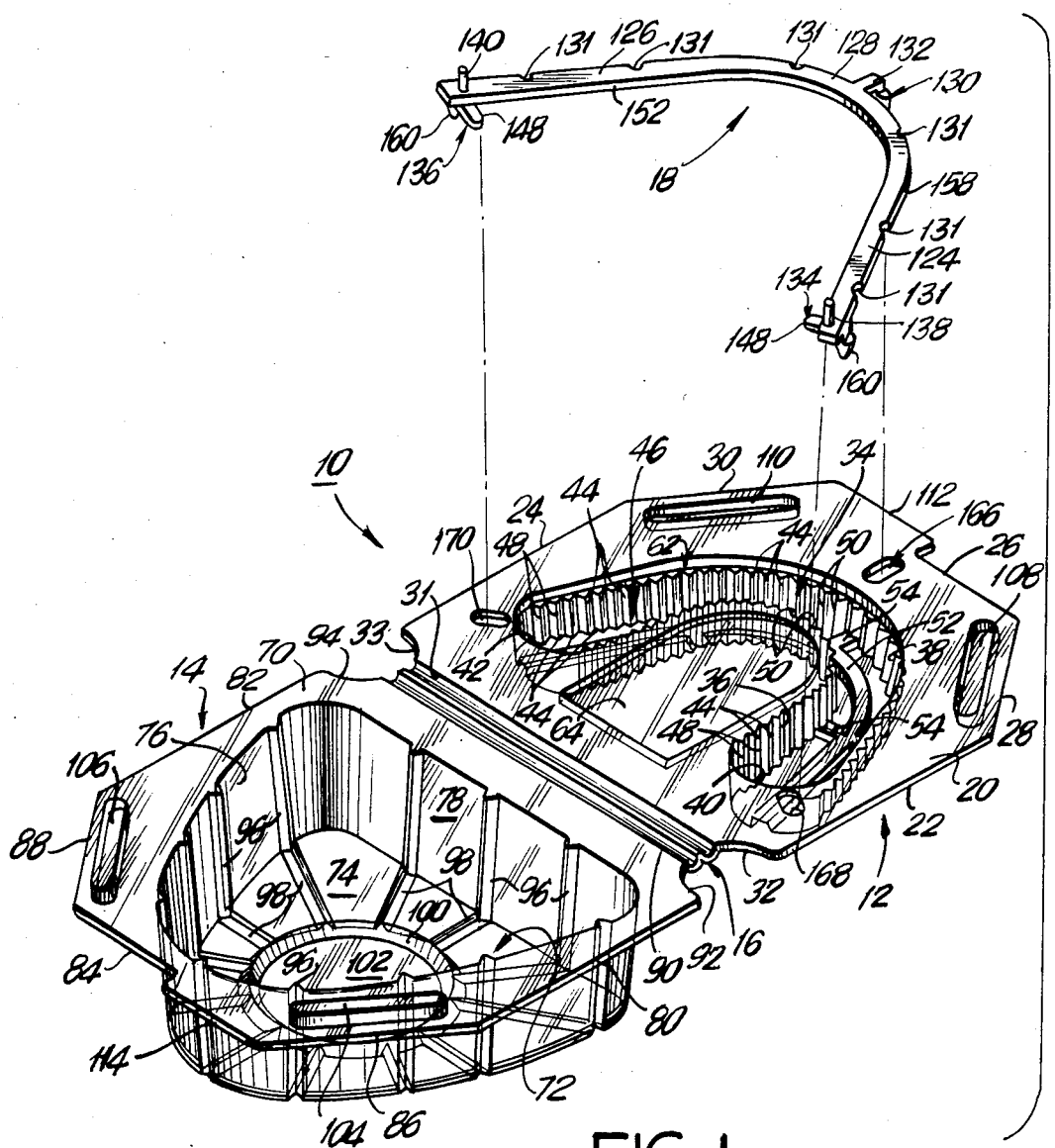
FIG. 1 is a perspective exploded view of the protective dental model carrier in an opened position, showing the arcuate U-shaped rib spaced above the tray portion.

Referring now to FIG. 1, there is shown a dental model carrier 10, preferably of transparent plastic, having a tray portion 12 and a cover portion 14 interconnected by means of an integral hinge 16. An arcuate U-shaped retaining member or rib 18, preferably of resilient plastic, is provided which will be received on the tray portion 12 for locking a dental model in place in the tray portion 12.

The tray portion 12 includes an upper planar top wall 20 of substantially rectangular configuration including the side edges 22, 24 interconnected to a distal free edge 26 by means of tapered corners 28, 30. The opposite inner edge 31 is interconnected to the integral hinge 16. Arcuate notches 32, 33 are formed at the corners of the inner edge 31.

A recessed cavity 34 depends from the top wall 20. The pedestal portion of the dental model will be received within the cavity 34. Such cavity 34 can be smooth or can include a keyed arrangement as shown in FIG. 1 to properly seat a keyed pedestal portion. Such keyed arrangements are well known. By way of example, a keyed arrangement for a dental model is described in U.S. Pat. No. 4,538,987 issued to the assignee of the present invention on Sept. 3, 1985. In such patent, there is described a dental die tray which includes a keyed arrangement having a plurality of corrugations, teeth or ribs, which will be cast directly into the pedestal portion of the dental model. A mating keyed arrangement can therefore be included into the dental carrier tray of the present invention.

The cavity 34 has an arcuate U-shape and includes an inner wall 36 and an outer wall 38 interconnected at the respective ends by rounded interconnecting walls 40, 42 to provide the U-shaped configuration. The arcuate inner and outer walls 36, 38 include corrugations or teeth 44 which protrude into the cavity chamber 46. The teeth 44 are of uniform projection, but certain sets of teeth can be wider than others. Specifically, the radius of the teeth at the distal ends 48 adjacent the interconnecting walls 40, 42 is larger than the radius of the teeth at the medial bight section 50. The cavity chamber 46 tapers outwardly as it progresses from the lower surface to the upper surface to form an outwardly flared cavity chamber whose upper end is wider than its lower end.

Formed at the bottom of the cavity chamber 46 and projecting upwardly from the base thereof, is an arcuate rib 52 including a plurality of laterally extending reinforcing webs 54. The rib 52 has opposing side surfaces which are downwardly sloped. However, the two sloped side surfaces can be at different angles and specifically, the outer slope facing wall 38 is steeper than the inner slope facing wall 36. The undersurface of the rib and the webs can be recessed as indicated at 60 in FIG. 8.

The outer wall 38 of the cavity chamber 46 is stepped just below the upper planar top wall 20 to provide a recessed seat 62 peripherally formed in a U-shape about the outer wall 38 of the cavity 34 and spaced below the top wall 20. A palate wall section 64 is formed between the leg portions of the inner wall 36 and extends toward the integral hinge 16.

The cover portion 14 includes a facial wall 70 from which depends a chamber 72. The chamber includes a base wall 74 with a substantially D-shaped side wall 76 closed off by an end wall 78. The facial wall 70 corresponds in shape to the upper top wall 20 of the tray portion 12 and includes the side edges 80, 82 interconnected to the distal free edge 84 by means of tapered corners 86, 88. The opposite inner edge 90 is connected to the integral hinge 16. Notched corners 92, 94 of the inner edge 90 extend to the integral hinge 16 from the side edges 80, 82.

Within the chamber 72, there is provided vertical stiffening ribs 96 which continue into radial stiffening ribs 98. These ribs 98 terminate in the center circular rib 100 defining a raised boss 102 on which there can be placed identification such as a self-adhesive label.

In order to lock the cover portion 14 onto the tray portion 12, there are provided projecting bosses 104, 106 adjacent the tapered corners 86, 88 of the cover portion 14. These bosses 104, 106 are received within correspondingly shaped hollow troughs 108, 110 extending down from the tray portion upper wall 20 adjacent the corresponding tapered corners 28, 30. When closed, the bosses 86, 88 enter into the hollow troughs 108, 110 and will be retained in place.

To facilitate opening of the carrier 10, the distal edge 26 of the upper wall 20 on the tray portion 12 has an outwardly projecting section 112. The corresponding facial wall 70 on the cover portion 14 also has an outwardly projecting section 114 offset from the projecting section 112 of the tray portion 12. In this manner, when the upper and facial walls 20, 70 abut each other in the closed position of the carrier tray, the two projecting sections 112, 114 will be non-mating. This will permit pulling the distal edges 26, 84 apart, so as to separate the cover portion 14 from the tray portion 12 and facilitate opening of the carrier tray.

Figure 6:
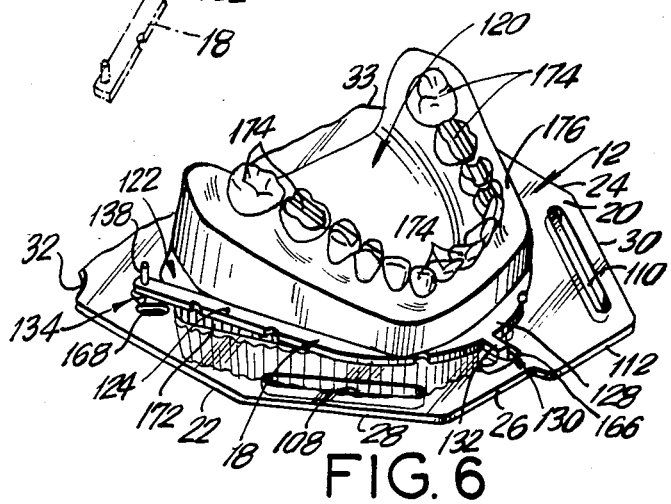
FIG. 6 is a fragmented perspective view of the tray portion, showing a dental model inserted into the tray portion with the arcuate rib oriented but not yet locked in place.

As can best be seen in FIG. 6, the dental model 120, which will be inserted into the tray portion 12, typically includes a peripheral ledge 122. Such ledge 122 is generally formed in the dental model 120 in order to facilitate its construction within the dental die tray. The formation of the dental model 120 is described in the aforementioned U.S. Pat. No. 4,538,987, which also describes the formation of the peripheral ledge 122.

Figure 7:
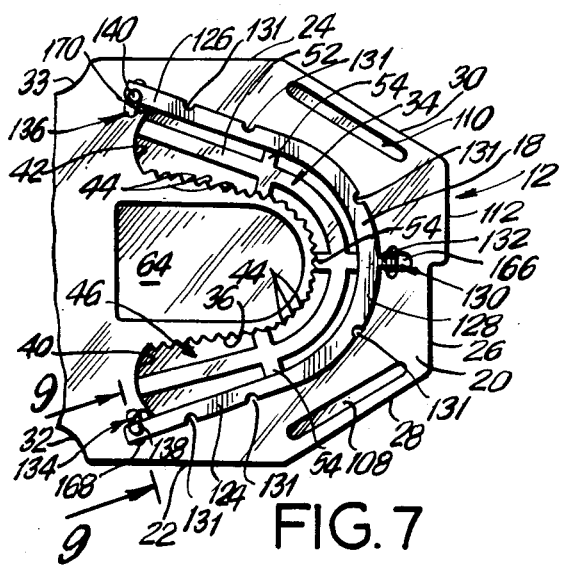
FIG. 7 is a fragmented plan view of the tray portion with the arcuate rib locked in place, the dental model having been removed from this figure only for the purpose of obtaining a better view of the overhang arrangement of the arcuate rib onto the cavity in the tray portion.

The retention of the dental model 120 in the tray portion 12 is achieved by utilizing this peripheral ledge 122. Specifically, the arcuate retaining rib 18 shown in FIG. 1 is positioned on the tray portion 12 so as to overhang the cavity in the tray portion 12, as best shown in FIG. 7, and thereby overlie the peripheral ledge 122 of a dental tray 120 when disposed within the cavity 34, as set forth below.

The arcuate U-shaped retaining rib 18 shown in FIG. 1 includes flared legs 124, 126 interconnected by a medial bight portion 128. A positioning tab 130 depends from the bight portion 128 and is retained by an extension arm 132. At the distal ends of the retaining rib 18 there are provided locking tab members 134, 136. Upwardly projecting handle posts 138, 140 at the distal ends are utilized to engage and disengage the locking tab members 134, 136 from the tray portion 12. Arcuate grooves 131 are formed in the rib 18 during molding to provide additional flexibility to the retaining rib 18. The rib 18 itself is preferably formed of plastic or can be metal, being bent in order to insert it onto the tray portion 12, as will hereinafter be explained.

Figure 2:
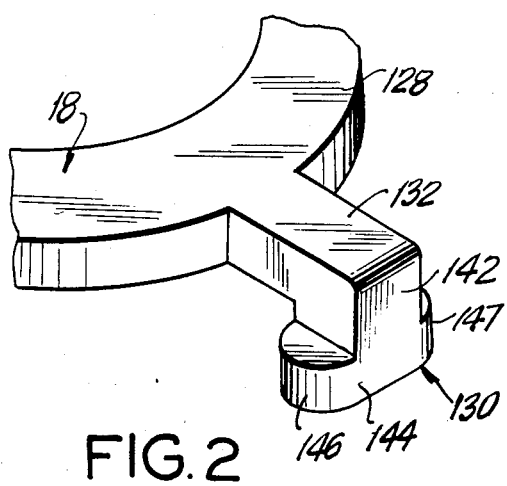
FIG. 2 is an enlarged fragmented perspective view of the positioning tab provided at the medial portion of the arcuate rib.

Referring now to FIG. 2, the positioning tab 130 is shown as an inverted T-shaped member including a depending leg 142 which depends from the retaining arm 132 at the bight portion 128 of the retaining rib 18. At the distal end of depending leg 142, is the transverse leg 144 including rounded edges 146, 147.

Figure 3:
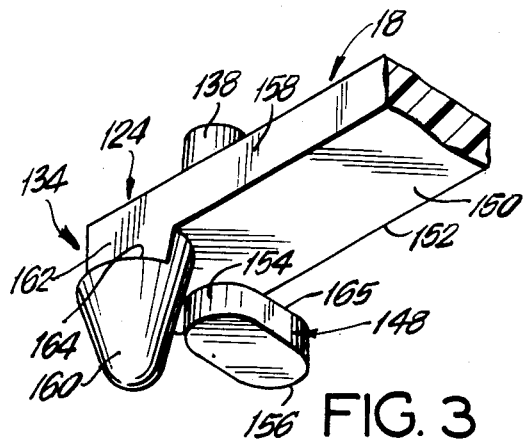
FIG. 3 is an enlarged fragmented perspective view of the underside of one distal end of the arcuate rib, showing the locking tab arrangement.

The locking tab member 134 is shown in FIG. 3 as depending from the distal end 124 of the retaining rib 18 and including a finger portion 148 connected to the underside 150 of the retaining rib 18. The finger portion 148 projects laterally from the inner side edge 152 of the rib 18 to extend inwardly from the arcuate shaped rib 18. The opposing ends 154, 156 of the finger 148 are rounded.

Projecting from the opposing outer side edge 158 of the retaining rib 18 is a depending frustroconical member 160. The member 160 laterally projects outwardly beyond the outer side edge 158. A notch 162 extends from the side edge 158 into the frustroconical member 160, terminating in an upper shoulder surface 164 which is at a lower planar level than the upper surface 165 of the finger 148, shown best in FIG. 9.

Figure 9:
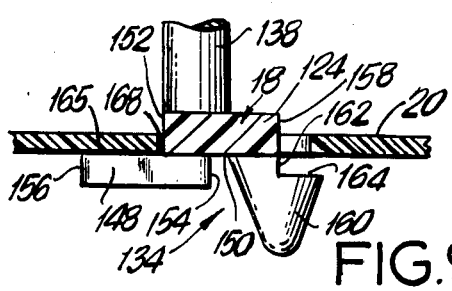
FIG. 9 is an enlarged cross sectional view taken along lines 9—9 of FIG. 7, showing the locking tab secured in its receiving slot.

Referring back to FIG. 1, an elongated slot 166 is provided through the top wall 20 of the tray portion 12 between the free edge 26 and the cavity 34 so that its elongated axis passes through the bight portion of the cavity 34 and will be perpendicular to the transverse direction of the leg 144 of the T-shaped positioning tab 130 when positioned therein. Adjacent the end walls 40, 42 of the cavity 34, there are likewise formed elongated slots 168, 170 for receiving the associated locking tab members 134, 136. It should be noted, that the elongated axes of the slots 168, 170 are at an angle to each other so that they extend from the end walls 40, 42 in a direction away from each other and will intersect or cross the axes of the fingers 148 of the locking tab members 134, 136 when positioned therein, as best shown in FIG. 7. It should also be noted, as can best be seen in FIG. 3, that the axis of each frustroconical member 160 passes through the elongated axis of its associated finger member 148. The distance from the round end 156 of the finger 148 to the notch 162 of the frustroconical member 160 is greater than the width of the slot 168, 170 which it crosses when the locking tab member 168, 170 is inserted therein, as shown in FIG. 9, as set forth below.

Figure 4:
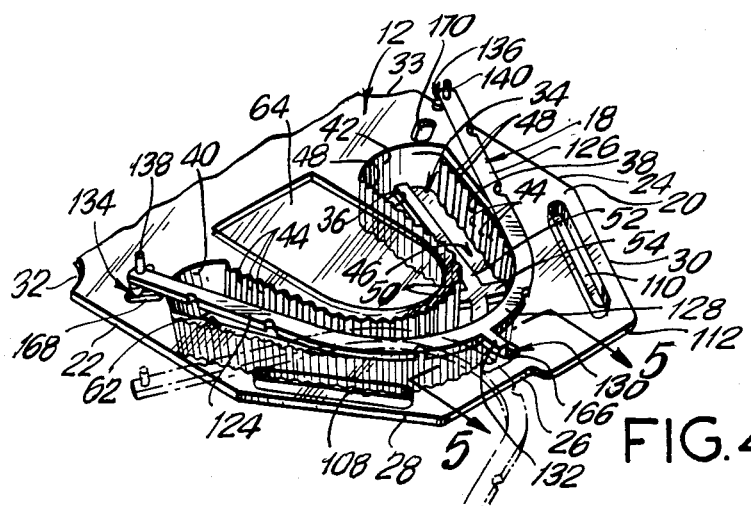
FIG. 4 is a fragmented perspective view of the tray portion, showing the interconnection of the positioning tab onto the tray portion as a first step in positioning the arcuate rib onto the tray portion.

Referring now to FIG. 4, there will be described a first step in the assembly of the retaining rib 18 onto the tray portion 12. The retaining rib 18 is initially turned 90 degrees, as shown by the dotted lines, in order to permit the transverse leg 144 of the T-shaped positioning tab 130 to be coaligned with the elongated axis of the slot 166. The transverse leg 144 can then be inserted through the slot 166 so that the leg 142 is in the slot 166 and the arm 132 is above the top wall 20.

Figure 5:
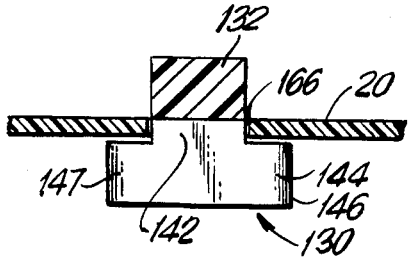
FIG. 5 is a cross sectional view taken along lines 5—5 of FIG. 4, showing the positioning tab oriented with respect to its receiving slot.

The retaining rib 18 is then rotated back 90 degrees to conform its arcuate shape with that of the cavity 34. In this way the inverted T-shaped positioning tab 130 is now secured in place, and the bight portion 128 of the rib 18 is held in position. The locking of the positioning tab 130 in the slot 166 beneath the top wall 20 is best shown in FIG. 5.

By pivoting the legs 124, 126 of the retaining rib 18 upwardly so that the arm 132 of the positioning tab 130 extends into the slot 166, the cavity 34 will be exposed to permit insertion of the dental model 120 therein, as shown in FIG. 6. The dental model 120 includes a pedestal portion 172 corresponding to the key shaped arrangement provided within the cavity 34. The pedestal portion 172 will properly seat within the cavity 34 and will snugly fit therein.

The dental model 120 includes the upwardly projecting teeth 174 and the gum area 176 which sit above the top wall 20 of the tray portion 12 and will be received within the chamber 72 provided in cover portion 14, as will hereinafter be explained.

With the dental model 120 now positioned in the tray portion 12, the legs 124, 126 of the retaining rib 18 can be pivoted down onto the ledge 122 of the model 120, being spread apart if required, so that the rib 18 can be secured by locking the locking tab members 134, 136 into their respective slots 168, 170.

The locking will now be described in connection with FIGS. 7 and 9. In FIG. 7, the dental model 120 would normally be in place as is shown in FIG. 6, however, the model 120 has been removed from FIG. 7 in order to obtain a better appreciation of the locking arrangement, and to better view the resulting overhang of the retaining rib 18 over the cavity 34 so as to overlie the ledge 122 provided on the dental model 120.

In order to lock the locking tab members 134, 136 into position, the distal ends of the legs 124, 126 are outwardly and downwardly twisted to permit insertion of each finger 148 into a slot 168, 170 beneath the top wall 20. With the finger 148 positioned beneath the top wall 20, the tip of each frustroconical member 160 extends into its associated slot 168, 170. The distal end of each leg 124, 126 of the retaining rib 18 is then pushed downwardly, using the posts 138, 140, so that the frustroconical members 160 will be forced through the slots 168, 170 to positions under the top wall 20, as shown in FIG. 9. The edges of the slots 168, 170 will slightly deform as the frustroconical members 160 are pressed downwardly to define a snap arrangement therebetween. Once the frustroconical members 160 are beneath the top wall 20, the notch 162 of each member 160 will seat itself under the top wall 20 so that the legs 124, 126 will be held in place. As shown in FIG. 9, the frustroconical member 160 has the upper surface 164 of its notch 162 at a plane lower than the upper surface 165 of the finger member 148. This will permit manipulation of the locking tab member 134 into the slot 168. The other locking tab member 136 would be likewise positioned within its slot 170.

With the positioning tab 130 and locking tab members 134, 136 in place, the retaining rib 18 overlies the ledge 122 and holds the dental model 120 in place. The cover portion 14 can be closed onto the tray portion 12, and the dental model 120 can be stored or transported securely.

Figure 8:
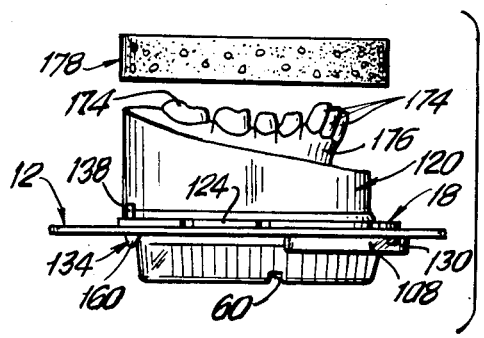
FIG. 8 is a fragmented elevational view of the protective carrier tray having a dental model secured in the tray portion, showing a foam pad which is used to hold the dental model in place within the carrier.

As shown in FIG. 8, the dental model 120 is secured into position in the tray portion 12, and is held in place by means of the retaining rib 18. In order to secure and further protect it, a pad 178 of foam material can be placed over the teeth 174. This provides a buffer or spacer when the cover portion 14 is closed onto the tray portion 12, where the pad 178 fills the remaining portion of the chamber 72 of the cover portion 14 which is not occupied by the dental model 120.

Figure 10:
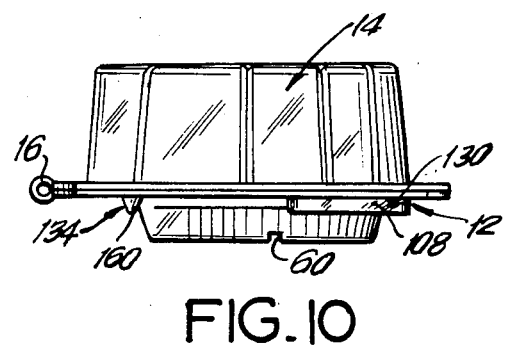
FIG. 10 is a side elevational view showing the protective carrier in a closed position.

The completed carrier 10 is shown in FIG. 10 with the cover portion 14 closed onto the tray portion 12, being securely locked together in place by means of the projected bosses 104, 106 received in the troughs 108, 110.

When it is desired to open the carrier 10 and remove the dental model 120, the sections 112, 114 are pulled apart to open the carrier 10. The retaining rib can be removed by pulling up on the handle posts 138, 140. The frustroconical portions 160 will deform the edges of the slots 168, 170 and be extracted from the slots 168, 170. The finger portions 148 can then be angularly lifted out through the slots 168, 170 from beneath the top wall 20. Pivoting the rib legs 124, 126 upwardly will give access to the dental model 120, whereby the dental model 120 can now be lifted up from the tray portion 12 and extracted from the protective carrier 10. If desired, the rib 18 can also be removed by rotating the rib the above mentioned 90 degrees to permit release of the positioning tab 130 from the slot 166 in the top wall 20.

There has been disclosed heretofore the best embodiment of the invention presently contemplated. However, it is to be understood that the present disclosure relates to a preferred embodiment of the invention which is for purposes of description only and is not to be construed as a limitation of the invention.

What is claimed is:

1. A protective carrier for a dental model having a pedestal part, comprising:
   a tray portion provided with a recessed cavity for receiving the pedestal part of the dental model;
   retaining means removably coupled to said tray portion for securing the dental model in said cavity;
   said retaining means including a rib member partially projecting over said cavity of said tray portion when coupled to said tray portion to thereby engage a ledge provided on the dental model to retain the dental model in said cavity;
   a cover portion provided with a recessed chamber for covering onto an upper portion of the detal model; and
   said chamber and said cavity mating to provide a closed compartment for the dental model when said cover portion is closed onto said tray portion.

2. A protective carrier as in claim 1, wherein said cavity of said tray portion and said rib member are arcuate in shape.

3. A potective carrier as in claim 2, wherein said cavity of said tray portion is U-shaped in planar configuration and has inner and outer U-shaped side walls, and wherein said rib member is U-shaped and overlies said outer side wall of said cavity.

4. A protective carrier as in claim 3, wherein said rib member is flexible.

5. A protective carrier as in claim 3, wherein said rib member includes a plurality of tabs, and said tray portion is provided with a plurality of slots for receiving said tabs to thereby retain said rib member in place on said tray portion.

6. A protective carrier as in claim 5, wherein one of said tabs is an inverted T-shaped tab member depending from a bight portion of said U-shaped rib member, and one of said slots is an elongated slot in said tray portion for receiving said T-shaped tab member, a longitudinal axis of said elongated slot lying perpendicularly to a transverse leg of said T-shaped tab member to provide a twist-lock retention of said bight portion of said rib member onto said tray portion.

7. A protective carrier as in claim 6, wherein said elongated slot is positioned between a free edge of said tray portion and said outer side wall of said cavity, and wherein an arm outwardly extends from said bight portion of said rib member for supporting said T-shaped tab member.

8. A protective carrier as in claim 5, wherein said rib member includes first and second leg portions, one of said tabs being disposed on a distal end of each of said first and second leg portions, and said slots including elongated receiving slots angularly oriented in an opposing direction to said tabs on said first and second leg portions to provide a snap-fit retention arrangement therebetween.

9. A protective carrier as in claim 8, wherein each said leg portion tab includes an elongated finger portion extending from an underside of said rib member and transversely projecting from one side edge of said rib member to anchor beneath a top wall of said tray portion after passing through its associated receiving slot, and a frustroconical snap member depending from said underside of said rib member and transversely projecting from the other side edge of said rib member to snap-fit into said associated receiving slot, said finger portion and said frustroconical snap member being coaxially arranged.

10. A protective carrier as in claim 9, wherein each said frustroconical snap member includes a downwardly directed notch extending from said other side edge of said rib member to permit seating beneath said top wall.

11. A protective carrier as in claim 10, wherein an upper shoulder surface of each notch lies in a lower plane than an upper surface of said finger portion.

12. A protective carrier as in claim 11, wherein an elongated axis of each receiving slot angularly crosses an axis extending through said finger portion and said frustroconical snap member.

13. A protective carrier as in claim 8, and comprising a handle post projecting upwardly from said distal end of said first and second leg portions to engage and disengage said leg portion tabs from their associated receiving slots.

14. A protective carrier as in claim 9, wherein said finger portions project inwardly toward each other.

15. A protective carrier as in claim 1, wherein said tray portion includes a substantially flat top wall with said cavity being recessed from said top wall, and said cover portion includes a substantially flat facial wall with said chamber being recessed from said facial wall, said facial and top walls mating in a closed position of said protective carrier, at least one raised boss being provided on one of said facial and top walls, and a correspondingly shaped trough provided in the other of said facial and top walls for receiving said boss, said boss locking into said trough to retain said closed position of said protective carrier.

16. A protective carrier as in claim 15, wherein said top wall and said facial wall are correspondingly shaped, each including an inner edge and an opposing distal free edge, and integral hinge means connected to said inner edge of each of said top and facial walls to connect said tray and cover portions together.

17. A protective carrier as in claim 16, wherein each said distal free edge of said top wall and facial wall is stepped to provide non-overlapping extensions for facilitating opening of said carrier.

18. A protective carrier as in claim 1, wherein said cavity of said tray portion includes keyed slot means for matingly engaging key means provided on the pedestal post of the dental model.

19. A protective carrier as in claim 1, wherein said cavity of said tray portion has a substantially U-shaped planar configuration including facing outer and inner arcuately shaped cavity walls interconnected by rounded end walls, and continuous teeth being disposed on said facing outer and inner cavity walls, said teeth extending into said cavity.

* * * * *